United States Patent [19]

Reinhart et al.

[11] Patent Number: 5,189,915
[45] Date of Patent: Mar. 2, 1993

[54] SINGLE MODE ULTRASONIC INSPECTION METHOD AND APPARATUS

[75] Inventors: Eugene R. Reinhart, Austin; Ronald E. Larsen, Del Valle; Michael C. Monaco; Teodoro Leon-Salamanca, both of Austin, all of Tex.

[73] Assignee: Reinhart & Associates, Inc., Austin, Tex.

[21] Appl. No.: 616,849

[22] Filed: Nov. 21, 1990

[51] Int. Cl.$^5$ ............................................. G01N 29/10
[52] U.S. Cl. ......................................... 73/623; 73/628
[58] Field of Search .................. 73/598, 623, 624, 628, 73/641, 612, 614, 625

[56] References Cited

U.S. PATENT DOCUMENTS

| | | |
|---|---|---|
| 3,508,436 | 4/1970 | Krautkramer . |
| 3,600,613 | 8/1971 | Clarke . |
| 3,683,680 | 8/1972 | Johnson et al. ........................ 73/628 |
| 3,712,119 | 1/1973 | Cross et al. . |
| 3,820,387 | 6/1974 | Grabendorfer et al. . |
| 3,845,463 | 10/1974 | Timbs . |
| 3,942,361 | 3/1976 | Rath et al. ............................. 73/624 |
| 3,952,581 | 4/1976 | Gottelt . |
| 3,960,006 | 6/1976 | Smith . |
| 3,999,422 | 12/1976 | Lehmann et al. . |
| 4,304,134 | 12/1981 | Rouse et al. . |
| 4,453,410 | 6/1984 | Schmitz et al. ........................ 73/623 |
| 4,523,468 | 6/1985 | Derkacs ................................ 73/598 |

Primary Examiner—John E. Chapman
Attorney, Agent, or Firm—Shaffer & Culbertson

[57] ABSTRACT

An ultrasonic inspection apparatus is adapted for utilizing both pitch/catch and pulse/echo information obtained utilizing a single mode of wave propagation. The apparatus includes an ultrasonic signal transmitting assembly, a signal receiving assembly, a positioning mechanism, and an arrangement for recording the information received by the signal receiving assembly. The transmitting assembly includes at least one source transducer for transmitting shear mode ultrasonic search signals into the mass of an object to be inspected. The signal receiving assembly receives shear mode ultrasonic catch signals that are produced as the ultrasonic search signals encounter discontinuities in the mass of the object to be inspected and are directed toward and detected by at least one catch transducer. The signal receiving assembly also receives shear mode ultrasonic echo signals that are directed back to a first source transducer. The position determining mechanism is adapted for controlling the position of each source transducer and each catch transducer and for keeping track of the exact position of each transducer as the transducers send and/or receive ultrasonic signals so that signals from common discontinuities may be grouped together or correlated. The recording device records the ultrasonic signals received by the signal receiving assembly in a form that enables the signals to be analyzed to help characterize the acoustic discontinuities in the mass of the object being inspected.

12 Claims, 6 Drawing Sheets

5,189,915

SINGLE MODE ULTRASONIC INSPECTION METHOD AND APPARATUS

BACKGROUND OF THE INVENTION

This invention relates to ultrasonic inspection methods and devices for performing such inspections, and particularly, to ultrasonic inspection methods and devices for inspecting turbine and generator rotors from the rotor bore surface.

Ultrasonic inspections are performed by directing ultrasonic signals into the mass of an object using a suitable transducer. Flaws in the material such as cracks, voids, or inclusions represent acoustic discontinuities that reflect a portion of the incident signal energy. The reflected portion of the signal is in some cases directed back to and may be detected by the transducer that generated the original signal. In other cases, some of the reflected energy may be directed off at an angle from the incident signal to a separate catch transducer capable of detecting the reflected signal. Utilizing the transmitting transducer as the detecting or pick-up transducer is commonly referred to as a pulse/echo inspection. Utilizing separate transmitting and receiving transducers is commonly referred to as a pitch/catch inspection.

Each transducer commonly comprises a piezoelectric element and is mounted in a block of suitable material to form a search unit. Upon receipt of a suitable voltage spike, each piezoelectric element transmits an ultrasonic signal into a material with which the search unit is in intimate accoustical contact. Conversely, upon receipt of a suitable ultrasonic signal from the material, each piezoelectric element produces a voltage signal proportional to the pressure amplitude of the ultrasonic signal incident on the element. The amplitude and shape of the voltage signal produced upon receipt of an ultrasonic signal reflected from a particular acoustic discontinuity (e.g. a flaw) provides information about the discontinuity. Also, the delay time of the returned signal relative to the transmitted signal, when coupled with information concerning the position and orientation of the search unit with respect to the part under inspection and information concerning the central rays or beams emitted or transmitted by the search unit or a separate pitch search unit, provides an indication of the location of the particular acoustic discontinuity.

In addition, the orientation of the piezoelectric element with respect to the surface of the material to be inspected determines both the direction of ultrasonic wave propagation in the material and the mode of wave propagation. When the piezoelectric element is parallel to the surface of the material to be inspected, that is, when the element is situated so that its planar faces are perpendicular or normal to the surface, the piezoelectric element produces ultrasonic waves in the material in the longitudinal mode. In the longitudinal mode, the particle motion in the host material is parallel to the direction of wave propagation. When the piezoelectric element is inclined at an angle to the surface of the material to be inspected greater than zero but less than the first critical angle, the element produces ultrasonic waves in the material in both the longitudinal and shear wave mode by the mode conversion process. Alternatively, when the piezoelectric element is inclined above the first critical angle with respect to the surface of the material to be inspected, the element produces by mode conversion shear mode waves travelling at a certain angle in the material with respect to the material surface. In particular, a piezoelectric transducer element inclined in a search unit at an angle greater than the first critical angle with respect to the surface of the material to be inspected completely suppresses the creation of longitudinal mode waves in the host material by mode conversion, leaving only shear mode waves propagating in the material. In the shear mode, the particle motion in the host material is transverse to the direction of wave propagation.

Ultrasonic inspection or testing techniques are used for detecting material flaws in a number of situations and are particularly valuable in detecting flaws in the material of turbine or generator rotors. Turbine and generator rotors containing certain types of flaws in their material may fail abruptly and catastrophically, particularly under the start-up rotational and thermal stresses. The flaws in the rotor material may grow over the course of the many start-up sequences and finally link up with each other to form cracks, some perhaps capable of unstable growth under stress. Cracks with dimensions greater than the critical size for unstable growth may cause the rotor to burst or fracture under rotational and thermal stresses present during a final start-up sequence of the rotor.

Since the risk of failure depends upon a number of characteristics of the particular flaws, any useful rotor inspection must not only detect and pinpoint the location of flaws but also provide information on flaw type, size, and orientation. U.S. Pat. No. 3,960,006 to Smith shows one apparatus for performing ultrasonic inspections of turbine or generator rotors. The device included a transducer carriage for positioning a number of transmitting and receiving transducers within the rotor bore, a mechanical system for keeping track of the positions of the transducers, and a recording system. Smith utilized multiple ultrasonic signals in different modes of wave propagation (i.e. longitudinal, shear, and surface wave modes) in an attempt to characterize flaws in the rotor mass. Shear mode waves were directed axially or circumferentially at various angles into the mass of the rotor to perform pulse/echo inspections. Also, longitudinal waves were directed generally normal to the rotor bore surface and detected by a separate transducer adjacent to the transmitting transducer to provide a pitch/catch inspection.

The longitudinal wave pitch/catch inspection device taught by Smith did not, however, provide an effective inspection of the near-bore rotor material. This inability to provide an effective search in the near-bore region arose from two phenomena which Smith failed to recognize. First, leakage of the transmitted signal into the adjacent receiving or catch transducer presented a strong standing indication that obscured signals actually produced by any acoustic discontinuity in the near-bore region. Secondly, the complex near-field pressure distribution produced by the transmitting transducer extended into the near bore region of the rotor material and interfered with the energy reflected from the flaws in the near-bore region.

Even in regions distant from the near-bore region the Smith inspection device had a serious shortcoming. The Smith device relied on combining indications from different modes of wave propagation in an attempt to characterize flaws in the rotor material. However, the angular dependencies of the amplitudes of scattered and reflected ultrasonic waves are dependent upon mode type and frequency as well as upon actual reflector or flaw characteristics. In particular, the polar distributions of the amplitudes of ultrasonic waves reflected, scattered, and defracted from a material discontinuity will, in general, vary considerably with the particle motion direction, wave length, and frequency of the waves that impinge on the discontinuity. Frequency is a strong determiner of attenuation but it is also a determiner of wavelength for a specified mode type since each mode type has an associated wave propagation velocity in a specified material. Because the amplitude of scattered and reflected ultrasound is not uniquely related to flaw characteristics, the characterization of flaws using amplitude data from multiple wave modes, as proposed by Smith, did not necessarily produce valid results. Specifically, even where the longitudinal wave pitch/catch inspection produced flaw indications, the information in such longitudinal wave indications could not necessarily be compared with the information obtained from the shear wave pulse/echo indications to reliably and accurately characterize flaws with respect to type, orientation, dimensions, and other parameters.

SUMMARY OF THE INVENTION

It is an object of the invention to provide an ultrasonic inspection device and method that overcomes the above-described problems and deficiencies and others associated with prior ultrasonic inspection devices and methods.

To accomplish these objects, an ultrasonic inspection device includes signal transmitting means including at least one source transducer and signal receiving means including at least one catch transducer. Position determining means serves to position each source transducer and each catch transducer with respect to the object being inspected so that the exact position of each transducer may be determined at any time during the inspection. The device also includes recording means capable of recording the signals received by the signal receiving means, the position of each transducer upon receipt of an ultrasonic signal, and the time interval between each transmitted signal and the received signals produced thereby.

According to the invention, the ultrasonic inspection device is adapted for producing both shear mode pulse/echo information and also shear mode pitch/catch information for acoustic discontinuities in the mass of the object being inspected. To obtain pulse/echo information, the receiving means is adapted for receiving shear mode ultrasonic echo signals detected or picked up by a first source transducer. These ultrasonic echo signals are produced as shear mode search signals transmitted from the first source transducer encounter acoustic discontinuities in the mass of the object and are reflected or otherwise directed back to the first source transducer. To produce shear mode pitch/catch information, the receiving means is adapted to receive those shear mode ultrasonic catch signals that are produced as shear mode search signals transmitted from a source transducer encounter discontinuities in the mass of the object and are directed away from the transmitting source transducer. Since these catch signals are directed away from the transmitting or source transducer, the signal receiving means includes at least one catch transducer for detecting the shear mode catch signals and preferably an array of catch transducers. The shear mode catch signals provide improved indications for near-bore flaws due to the greater separation between the transmitting or pitch source transducer and the detecting or catch transducer. Furthermore, the shear mode catch signals better correlate with the pulse/echo information, which is also obtained by inspection in the shear wave mode. Also, using data from only one wave mode simplifies analysis by removing wave velocity differences inherent in different wave modes.

In one form of the invention the inspection device not only provides shear mode pulse/echo and pitch/catch information, but is also adapted to receive and record both echo and catch signals produced from shear mode search signals emitted from a common source transducer. This preferred form of the invention includes at least one catch transducer adapted for detecting shear mode ultrasonic catch signals that are produced as the search signals from the first source transducer encounter acoustic discontinuities in the mass of the object and are directed away from the first source transducer. The echo and catch information produced from a common search signal enables the device to see any acoustic discontinuity from two separate perspectives without any discrepancies being introduced through discrepancies in search signals.

The source transducers and catch transducers are each contained in a suitable block of material or shoe. The combination of the transducer element or elements and the shoe forms a search unit. The search units are mounted on a suitable search module with their transducers in a desired orientation and the module is adapted to position the various search units adjacent to the object to be inspected so that the transducers may transmit ultrasonic search signals into the object material and receive flaw signals from the material. Although the search module may be manipulated by hand, the preferred position determining means includes drive means for moving the module along the surface of the object to be inspected while keeping track of the transducer position. Where the object to be inspected is a turbine or a generator rotor with a generally cylindrical rotor bore extending therethrough, the module is adapted to be inserted into the cylindrical bore and to press each search unit against the surface of the bore with a suitable mechanical biasing arrangement. The drive means for the rotor inspection device includes an extension member connected to the module and a motor coupled with the extension member for rotating the module within the bore and for advancing the module longitudinally through the bore by manipulating the extension member.

The recording means includes a suitable arrangement for recording the signals received or detected at the catch transducers and the source transducers. One form of the invention includes separate ultrasonic instruments for each transducer on the module adapted to detect the signals produced as the shear mode search signals encounter acoustic discontinuities in the material being inspected. The preferred instrument includes a cathode ray tube (CRT) screen for displaying the signal detected by its respective catch or source transducer. Since the ultrasonic signals displayed on the CRT screen are transient, the recording means in this form of the invention includes a suitable video camera for each CRT screen and suitable video recording means for recording all of the signals displayed on the ultrasonic instrument CRTs.

To avoid using several separate ultrasonic instruments, an alternate preferred recording means utilizes a digital computer to receive, store, and display the signals detected by the catch and source transducers. A printer or plotter is also employed to produce hard copies of the signals received by the computer.

In the computer display form of the invention, a multiplexer circuit is employed to sequentially pulse the source transducer or transducers and to monitor receiving circuits sequentially for receiving voltage signals indicative of the ultrasonic signals detected by the various catch and source transducers. The sequencing repitition rates are chosen to preclude any loss of data.

One preferred ultrasonic inspection device embodying the principles of the invention includes a plurality of source transducers for introducing search signals into the mass of the object in several different directions. The first source transducer is mounted on the transducer module so as to direct search signals axially, that is, along a plane extending radially from the longitudinal axis of the bore and at an angle of between approximately 40° to 60° to a plane tangent to the bore surface. An array of catch transducers are positioned on the module generally in the plane of the search signals from this axial first source transducer, with each catch transducer spaced away from the first source transducer so as to detect catch signals produced at a different depth range below the surface of the rotor bore.

This preferred rotor inspection device also includes another first source transducer positioned on the module so as to direct its search signals circumferentially, that is, along a plane substantially perpendicular to the bore longitudinal axis and at an angle between 40° to 60° to a plane tangent to the bore's surface. Several other circumferentially directed source transducers are positioned at different angular orientations about the module, each source transducer forming a pitch/catch pair with a single separate catch transducer. The angular difference between transducers in each pitch/catch pair and the angle at which the transducers direct or receive ultrasonic signals determines the effective depth of investigation for that particular pitch/catch pair. Several shear mode pitch/catch pairs are required in order to obtain a complete inspection of a thick-walled rotor.

These and other objects, advantages, and features of the invention will be apparent from the following description of the preferred embodiments, considered along with the accompanying drawings.

DESCRIPTION OF THE PREFERRED EMBODIMENTS

Figure 1:
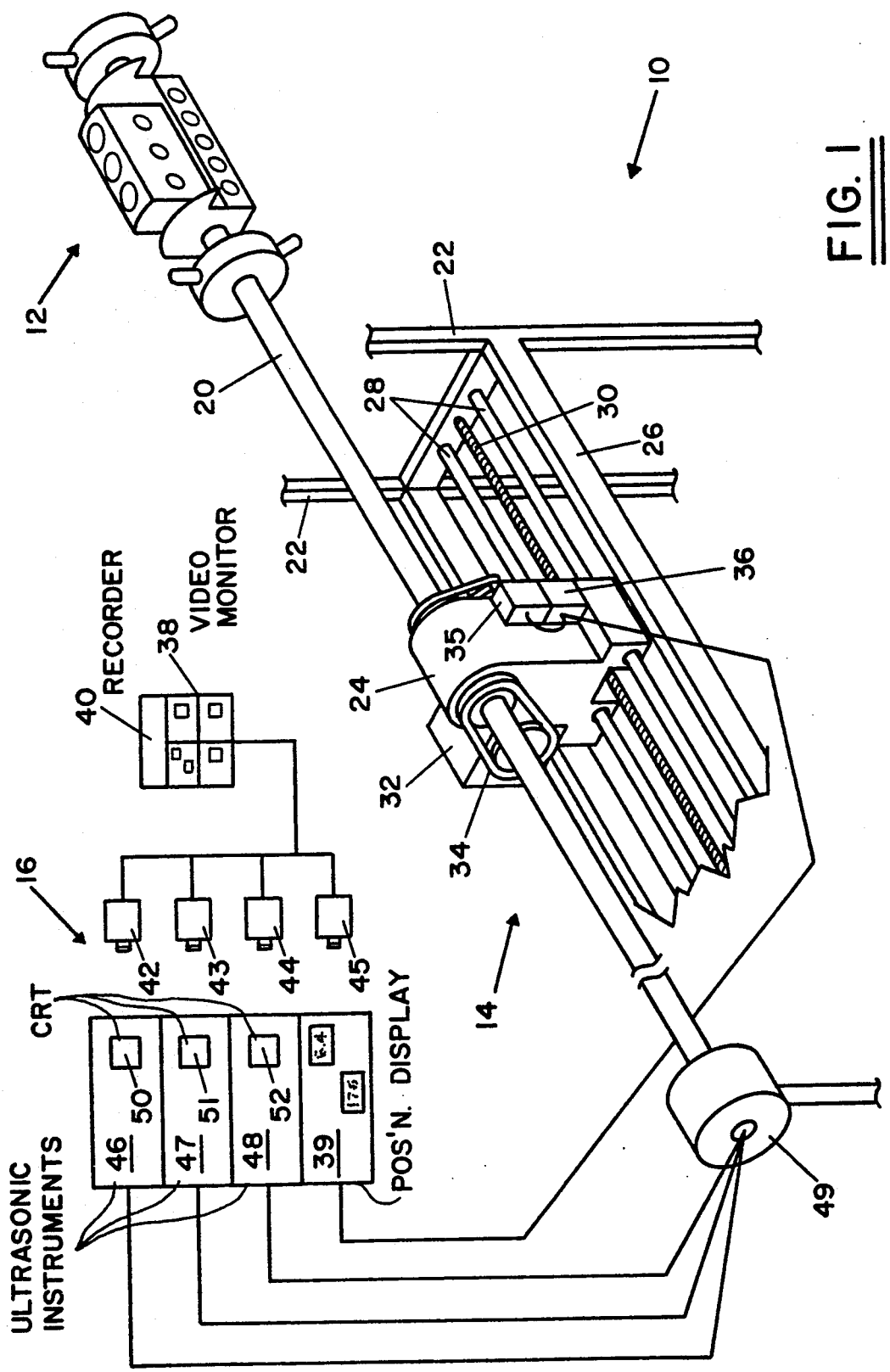
FIG. 1 is a somewhat schematic view in perspective of an ultrasonic inspection device embodying the principles of the invention.

An ultrasonic inspection device 10 embodying the principles of the invention is shown in FIG. 1. The device 10 includes a search module 12, position determining means 14, and signal recording means generally indicated at reference number 16. This particular embodiment of the invention is specifically adapted for providing ultrasonic inspections of objects having a bore extending at least partially therethrough such as generator or turbine rotors. Although the invention is described herein with reference to generator or turbine rotor inspection devices, those skilled in the art will readily appreciate that the inspection method and apparatus according to the invention may be employed in inspection devices other than those designed specifically for inspecting generator or turbine rotors.

The position determining means 14 shown in FIG. 1 is adapted for controlling the position of the module 12 with respect to the object being inspected, in this case a rotor (not shown), and includes search module drive means for manipulating the transducer module on a drive shaft 20. The illustrated drive means is adapted to connect to one end of the generator or turbine rotor with mounting brackets 22 and includes a shaft connecting structure 24 and a longitudinal support structure. The support structure comprises an elongated frame 26 extending from the mounting brackets 22, and two parallel rails 28 mounted within the frame along with an elongated advancing gear 30. The shaft connecting structure 24 is mounted on the rails 28 and is adapted to receive and firmly grip the drive shaft 20 while allowing the shaft to rotate about its longitudinal axis. A drive motor 32 is mounted on the shaft connecting structure 24 and is coupled to the drive shaft 20 by a suitable mechanical linkage 34 for rotating the drive shaft within the support structure and thereby rotating the search module 12. The drive motor 32 also drives a suitable gear (not shown) on the shaft connecting structure adapted to engage the elongated advancing gear 30 so as to advance the shaft connecting structure 24 and the shaft 20 longitudinally along the frame 26 as the motor is operated. Thus the drive means is adapted to simultaneously rotate and slowly advance the search module 12 to produce a spiral scan of the rotor to be inspected.

In addition to the drive means the position determining means 14 includes means for determining the angular and longitudinal position of the search module 12 as it is driven through the rotor bore. In FIG. 1, the position determining means 14 includes a rotational displacement encoder 35 and a longitudinal displacement encoder 36. Each encoder converts the movement of the drive shaft 20, and thus the search module 12, into a displacement from an index point and thereby provides an indication of the position of the search module with respect to the rotor at all times during an inspection.

The signal recording means 16 shown in FIG. 1 includes a video monitor 38, a video recorder 40 for recording the signals displayed by the monitor, and three separate video cameras 42, 43, and 44. Each video camera 42, 43, and 44 is adapted to continuously record the operation of a different ultrasonic instrument 46, 47, and 48, respectively, and particularly the CRT screen display 50, 51, and 52 of the respective ultrasonic instrument. The signal recording means 16 also includes a position display device 39 for digitally displaying the angular and longitudinal displacement information provided by the encoders 35 and 36. A fourth video camera 45 records the displacement information from the device 39. In order to accommodate the four separate video camera signals, the video monitor includes a screen splitting device (not shown) for dividing the screen of the monitor into four discrete sections. The separate video camera signals are then displayed individually and simultaneously in separate screen sections. The ultrasonic instruments 46, 47, and 48, which may, for example, be MARK IV instruments by Sonic Instrument Company, are electrically coupled to the search module 12 through a slip ring assembly 49 since the module is adapted to be operated in a continuous spiral scan.

Figure 2:
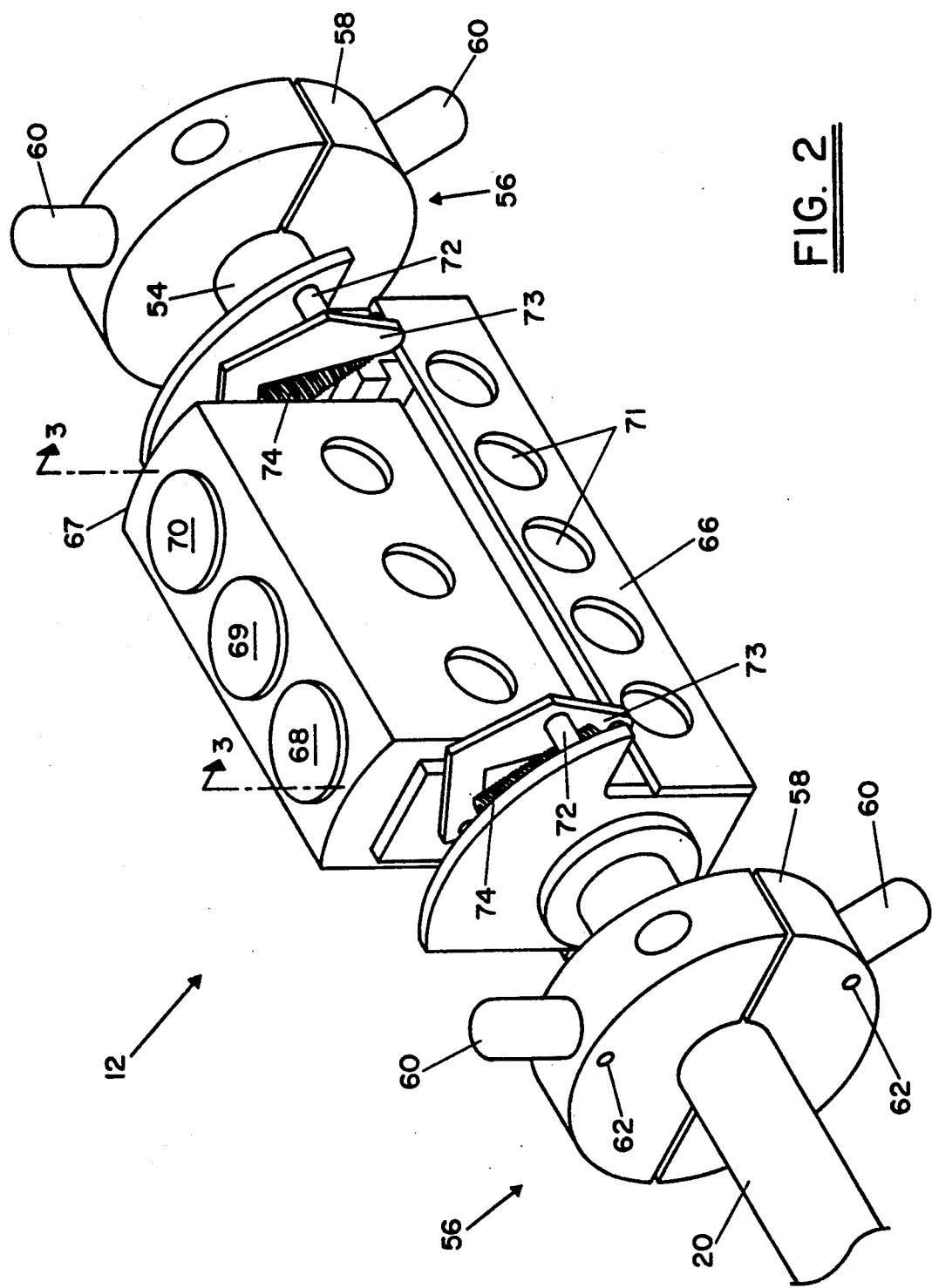
FIG. 2 is a view in perspective of the search module shown in FIG. 1.

Referring now particularly to FIG. 2, the search module 12 is adapted to connect to one end of the drive shaft 20 and includes a shaft extension 54 at the end opposite to the end connected to the drive shaft. A centering donut 56 is connected to the shafts 20 and 54 at each end of the module 12 for centering the module within the rotor bore. Each centering donut 56 includes a split collar 58 adapted to connect to and grip the respective shaft, and three dowels 60 extending from the collar at 120° intervals. The dowels 60 are preferably made from a suitable soft material such as NYLON so as to prevent damage to the bore surface and are received in radially extending dowel receptacles formed in the split collars. Suitable set screws 62 are preferably used to set the dowels 60 at a desired centering length.

The search module 12 includes a base member 66, a housing 67 mounted on the base member, and a plurality of search units 68, 69, and 70 mounted on the housing, each search unit carrying one or more transducer elements. The base member 66 is connected at one end to the drive shaft 20 and at the other end to the extension shaft 54 and comprises an elongated rectangular box made of a suitable lightweight material such as aluminum with lightening holes 71 for reducing the overall weight of the device. The housing 67 comprises an elongated rectangular block of material adapted to fit in the top opening of the box comprising the base member 66, and is preferably connected to the base member with a suitable biasing arrangement for biasing the housing upwardly in the figure and toward the wall of the rotor bore in use. The preferred biasing arrangement includes L-shaped pivot member 73 pivotally connected to the base member 66 at each end on pivot connections 72. A biasing spring 74 biases the lower end of each pivot member 73 inwardly and thereby forces the top of the pivot members 73 upwardly along with the housing 67. Each search unit 68, 69, and 70 is received in a separate opening formed in the housing 67 and is also preferably biased radially outwardly (upwardly in FIG. 2) by a suitable biasing spring (not shown) within the housing.

The biasing arrangement of both the housing 67 and each of the individual search units 68, 69, and 70 mounted in the housing helps ensure continuous contact between the surface of the search units and the surface of the rotor bore. Such contact is required in order to produce good acoustic coupling between the transducers located within the search units and the bore surface. Also, a bath of oil or other suitable liquid is preferably maintained along the bottom of the rotor bore to provide a film of the liquid on the search units and the bore surface to further maintain good acoustic coupling to the bore surface.

Figure 3:
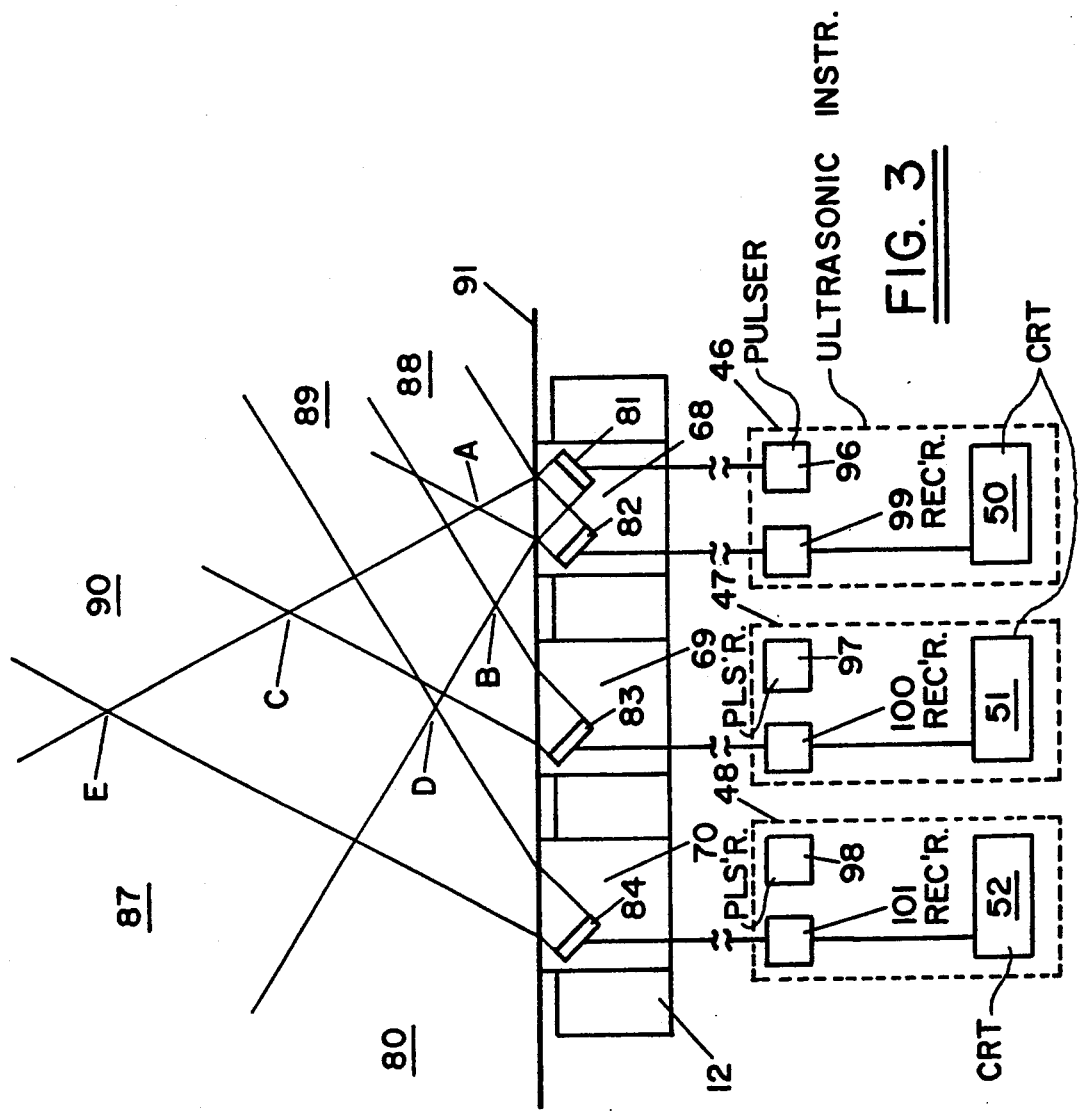
FIG. 3 is a schematic representation in longitudinal section taken along line 3—3 in FIG. 2.

The embodiment of the invention shown in FIG. 1 is adapted to provide a complete ultrasonic inspection according to the method of the invention by making three separate passes through the rotor bore, each pass with a different transducer arrangement. FIG. 3 illustrates one transducer arrangement that may be employed in an inspection according to the method of the invention. Each search unit 68, 69, and 70 includes at least one ultrasonic transducer for directing ultrasonic signals into the rotor material 80 or for picking up or detecting ultrasonic signals from the rotor material. However, each transducer in the device is adapted for producing or detecting only shear mode ultrasonic signals that travel at a particular angle through the material.

As shown in FIG. 3, search unit 68 includes a first source transducer or pitch transducer 81 oriented for directing shear mode ultrasonic search signals axially through the rotor material 80, that is, in a plane extending substantially radially from the longitudinal axis of the rotor bore. A separate catch transducer 82 is also mounted in the search unit 68 in position to receive ultrasonic signals that are produced as the search signals transmitted by the transducer 81 encounter acoustic discontinuities in the rotor material and are reflected or otherwise directed toward the catch transducer. The two other search units 69 and 70 in the module 12 also have catch transducers 83 and 84, respectively, oriented to receive catch signals produced as the signals transmitted from the source transducer 81 encounter acoustic discontinuities in the rotor material 80 and are reflected axially.

Each of the catch transducers 82, 83, and 84 shown in FIG. 3 is positioned for detecting catch signals reflected or otherwise produced from different depth intervals of the rotor material 80. The useful depth range for each catch transducer 82, 83, and 84 is defined by the radial distance over which the boundaries of the far-field diffraction pattern of each catch transducer overlaps with the diffraction pattern of the source or pitch transducer 81. The diffraction pattern of the source transducer 81 in FIG. 3 is schematically illustrated at reference numeral 87 and the diffraction pattern for each catch transducer 82, 83, and 84 is shown at reference, numerals 88, 89, and 90, respectively. The diffraction pattern 88 for the catch transducer 82 overlaps the diffraction pattern 87 for the source transducer 81 from generally the surface 91 of the bore out to Point A in FIG. 3. The diffraction pattern 89 of catch transducer 83 overlaps the source transducer diffraction pattern 87 from the depth shown at Point B to the depth at Point C and the overlap for the catch transducer 84 is from Point D to Point E. Thus, as the transducer module 12 travels longitudinally through the rotor bore, the combination of the single source transducer 81 and three separate receiving or catch transducers 82, 83, and 84 provides information on acoustic discontinuities located from near the bore surface 91 out to the depth at Point E. Although three separate catch transducers are shown for the sake of explanation, it will be appreciated that more or fewer catch transducers may be required for a desired total depth of investigation.

Each search unit 68, 69, and 70 may be made of a suitable acrylic plastic material with the transducer element embedded in the plastic material along with its connecting electrical lines as is known in the art. Each transducer element 81, 82, 83, and 84 in the preferred form of the invention comprises a piezoelectric element adapted to distort under an applied voltage signal to produce an ultrasonic signal in the plastic and then the rotor bore material. Upon receipt of an ultrasonic signal the piezoelectric material flexes and induces an electrical voltage signal indicative of the received ultrasonic signal.

As shown in FIG. 3, a suitable pulser circuit 96 supplies the electrical signal for exciting the source transducer 81 to produce the ultrasonic search signal having the diffraction pattern 87. An electrical signal produced by the first catch transducer 82 upon receipt of an ultrasonic catch signal is directed to a receiving circuit 99 for conditioning and transmission to a suitable display or recording device. Similarly, the second catch transducer 83 directs its received signal to receiver circuit 100 and the third catch transducer directs its signal to the receiver circuit 101.

Each of the receiver circuits 99, 100, and 101 forms part of a different one of the ultrasonic instruments 46, 47, and 48, also shown in FIG. 1. Each ultrasonic instrument also includes a pulser circuit 96, 97, and 98, although only the pulser 96 in the instrument 46 is utilized in the transducer arrangement shown in FIG. 3. The signals received and conditioned by the receiver circuits 99, 100, and 101 are displayed on the CRT screens 50, 51, and 52, respectively, and such signals are recorded with the video camera arrangement shown in FIG. 1.

The piezoelectric elements of the transducers shown in FIG. 3 are each oriented at an angle of approximately 38° to the normal to the surface of the bore to produce divergent beams of refracted shear wave ultrasound that have central rays oriented at an angle of approximately 45° with respect to the normal to the bore surface. By the reciprocity theorem, transducers that serve as receivers rather than transmitters of ultrasound also have divergent sensitivity or reception patterns. Although the 38° piezoelectric element orientation is preferred, other angular orientations of piezoelectric elements beyond first critical angle may be used according to the invention. Also, the second and third search units 69 and 70 may contain two separate catch transducer pieoelectric elements oriented at different angles to the bore surface. In one alternate form of the invention, the second and third search units may each include 40° and 50° refracted shear wave transducer elements to provide more overlap of information in the effective search range, the separate transducers providing overlapping and confirming information regarding discontinuities in the rotor material.

In addition to the scan of the rotor using the transducer arrangement shown in FIG. 3, the method of the invention also includes scanning the rotor to produce shear mode pulse/echo information regarding acoustic discontinuities. This pulse/echo information is recorded by means similar to those used to record the catch information and may be correlated with the catch information in the same mode and combined with the catch information to provide an indication of flaw characteristics. For example, the first search unit 68 in FIG. 2 may include a transducer (not shown) to direct ultrasonic search signals circumferentially and clockwise within the rotor material and the second search unit 69 may include a transducer oriented to direct signals circumferentially and counterclockwise. The third search unit 70 may be disconnected or may include an axially directed transducer element. The preferred ultrasonic inspection using the apparatus shown in FIG. 1 and 2 also includes a scan employing axially directed forward and aft pulse/echo transducer elements mounted in any two of the three search units on the module. In each case each transducer element employs both the pulser and receiver of one of the ultrasonic instruments for pulse/echo operation as is commonly known in the art.

Figure 4:
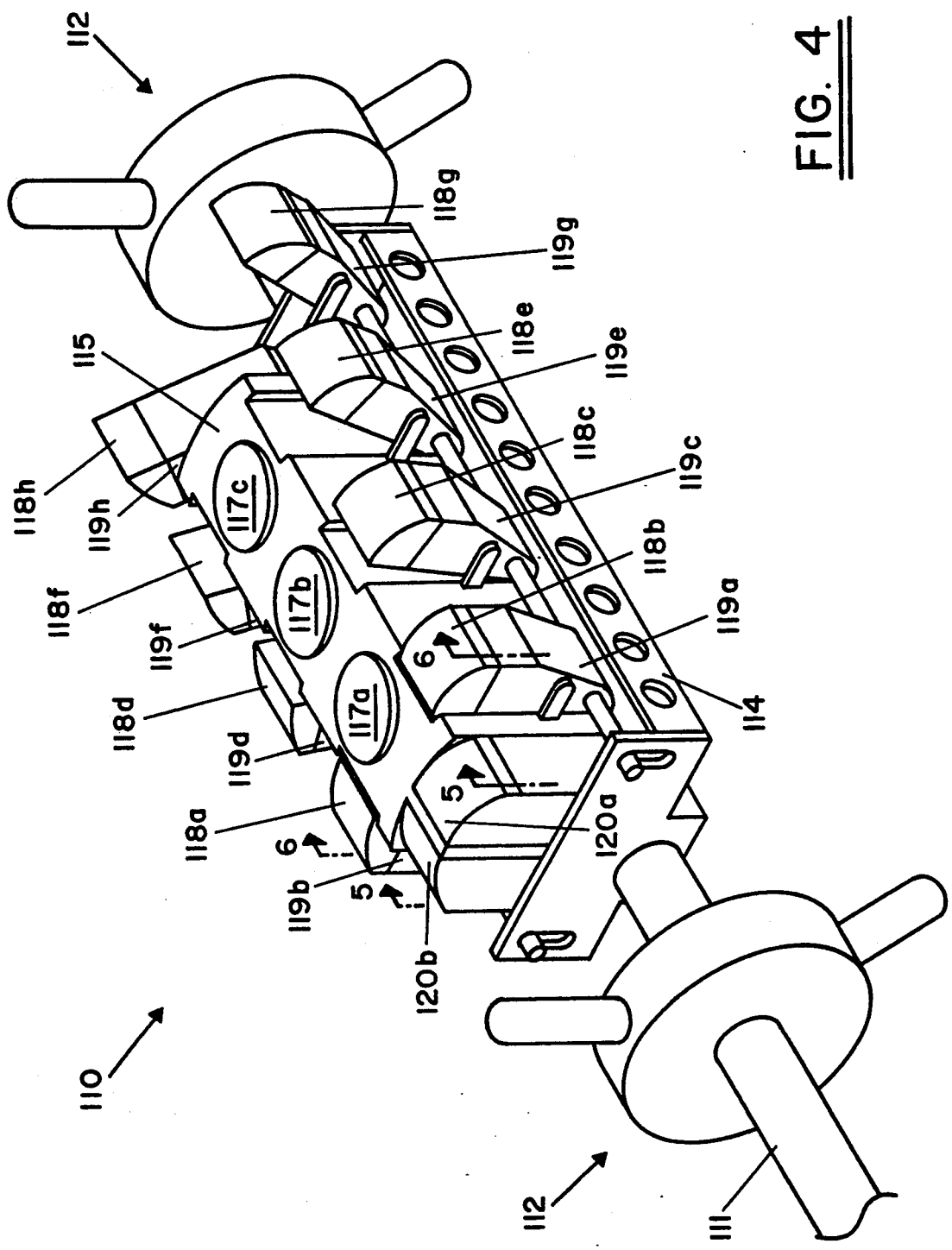
FIG. 4 is a view in perspective of an alternate search module for use in an ultrasonic inspection device embodying the principles of the invention.

Although the device 10 shown in FIG. 1 utilizing the three-search unit module 12 may be employed to perform ultrasonic inspections according to the method of the invention, inspections with the three-search unit module requires changing out the search units and making multiple passes through the rotor bore. FIG. 4 shows an alternate search module 110 that is adapted for performing a complete ultrasonic inspection according to the method of the invention in a single pass through a rotor bore. The alternate search module 110 is connected to a drive shaft 111 similar to the shaft 20 shown in FIG. 1 and includes centering donuts 112 at either end for centering the module in the rotor bore. The module 110 comprises a base 114 and an upwardly biased housing 115 also similar to the base 66 and housing 67 shown in FIG. 2. Three axially aligned search units 117a–c are mounted on the housing 115 with axially oriented transducers as will be described below.

Unlike the search module 12 shown in FIG. 1, the module 110 shown in FIG. 4 includes a number of laterally spaced search units 118a–h mounted on separate lateral housings 119a–h connected along either side of the main housing 115. The module 110 also includes a pair of laterally spaced search units 120a–b at one end of the housing 115. Each laterally spaced search unit is mounted on a suitable biasing spring (not shown) within its particular housing and is held by its housing at a desired angular orientation about the circumference of the rotor bore with respect to the remainder of the laterally spaced search units. Also, each of the laterally spaced search units 118a–h is transversely aligned with another of the laterally spaced search units mounted on the opposite side of the housing 115.

Figure 6:
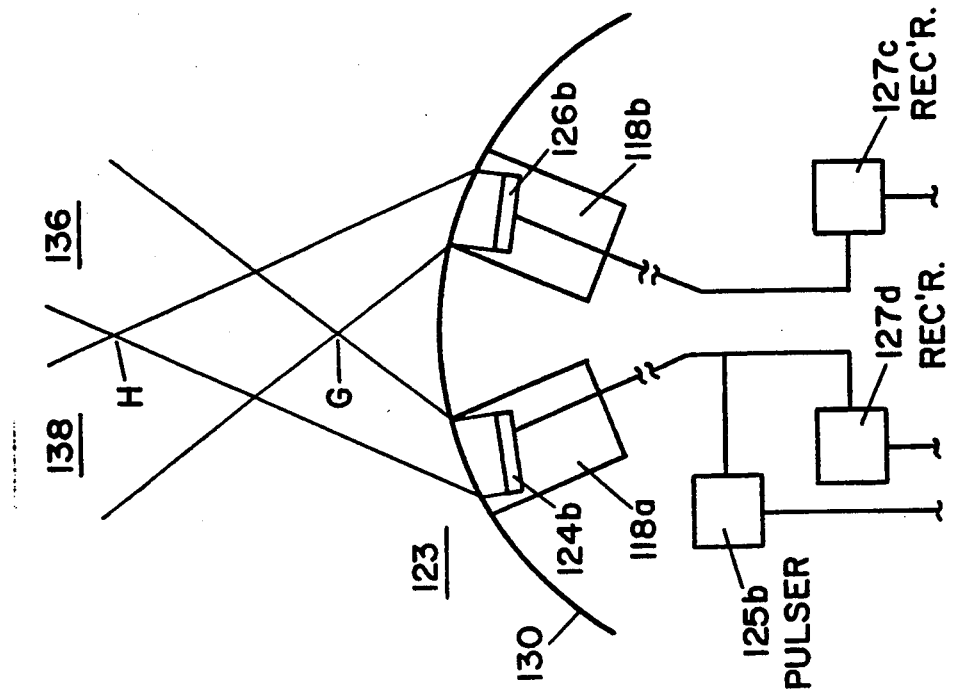
FIG. 6 is a schematic representation in transverse cross section taken along line 6—6 in FIG. 4.
Figure 5:
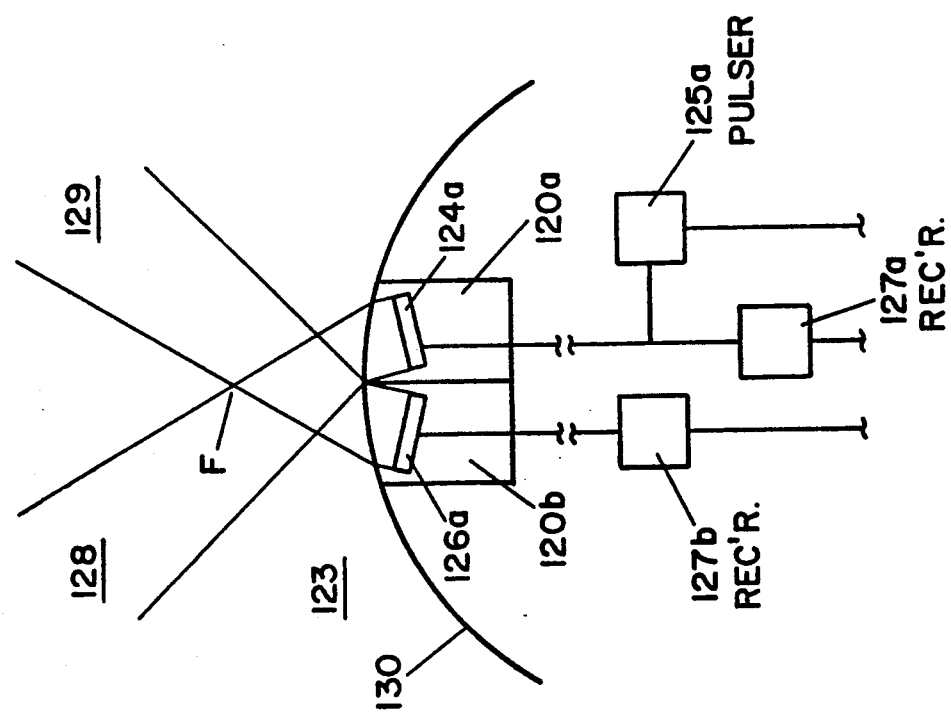
FIG. 5 is a schematic representation in transverse cross section taken along line 5—5 in FIG. 4.

FIGS. 5 and 6 schematically show the first two transversely aligned sets of laterally spaced comprising search units 120a–b and 118a–b at the left end of the module 110 shown in FIG. 4. As shown in FIG. 5, the right side search unit 120a of the most narrowly spaced search unit pair includes a first source transducer element 124a connected to a pulser circuit 125a and oriented for directing ultrasonic search signals circumferentially into the rotor material 123 in a counterclockwise direction. The left side search unit 120b includes a catch transducer element 126a connected to a receiver circuit 127b and oriented for receiving circumferentially directed ultrasonic catch signals produced as the search signals transmitted from the source transducer 124a encounter acoustic discontinuities in the rotor material. The effective depth range of this circumferential pitch/catch pair is defined by the area of overlap in the diffraction pattern 128 produced by the source transducer 124a and the diffraction pattern 129 associated with the catch transducer 126a. As shown in FIG. 5 the area of overlap extends substantially from the bore surface 130 to the depth indicated at Point F.

Referring now to FIG. 6, the left search unit 118a of the second laterally spaced search unit pair includes a source transducer element 124b connected to a suitable pulser circuit 125b and oriented to direct ultrasonic search signals circumferentially into the rotor material 123 in a clockwise direction and in a diffraction pattern shown at reference numeral 136. The right search unit 118b includes a catch transducer element 126b oriented to detect ultrasonic catch signals produced as the search signals transmitted by source transducer 124b encounter acoustic discontinuities in the rotor material 123. The diffraction pattern associated with the catch transducer 126b is shown at reference numeral 138 overlapping with the diffraction pattern 136 which results in an effective inspection depth range from Point G in FIG. 6 to Point H.

The difference in effective inspection depth between the transducers shown in FIG. 5 and the transducers shown in FIG. 6 is produced by the wider lateral or angular spacing between the respective transducer elements. By choosing the spacing between the transversely aligned and laterally spaced search units 118a-h and 120a-b so that their effective inspection depths overlap, several transversely aligned sets, each with a relatively small effective inspection range, may be combined to provide an overall inspection of a thick-walled rotor. Referring again to FIGS. 5 and 6, the two sets of transversely aligned search units 118a-b and 120a-b provide an overall effective depth of investigation from substantially the bore surface 130 to the depth at Point H. The remaining sets of lateral spaced search units 118c-h similarly include search and catch transducers arranged and spaced to provide an overall effective inspection depth throughout the rotor material.

As also shown in FIG. 5 the first source transducer element 124a is also connected to a receiver circuit 127a and is capable of receiving ultrasonic echo signals produced as the ultrasonic search signals that the element transmits encounter acoustic discontinuities in the rotor material 123 and are directed back to the source transducer 124a. Similarly the first source transducer element 124b shown in FIG. 6 is also connected to a receiver circuit 127d and is capable of receiving echo signals produced from its transmitted search signals. Thus, the transducer arrangement shown in FIGS. 5 and 6 produces not only circumferential pitch/catch information using shear mode ultrasonic waves, but also produces circumferential pulse/echo information in both the clockwise and counterclockwise directions. Furthermore, the circumferential pitch/catch and pulse/echo information produced by the transducer arrangements shown in FIGS. 5 and 6 may be acquired using a single incident or search ultrasonic signal transmitted by the source transducer elements 124a and 124b.

Figure 7:
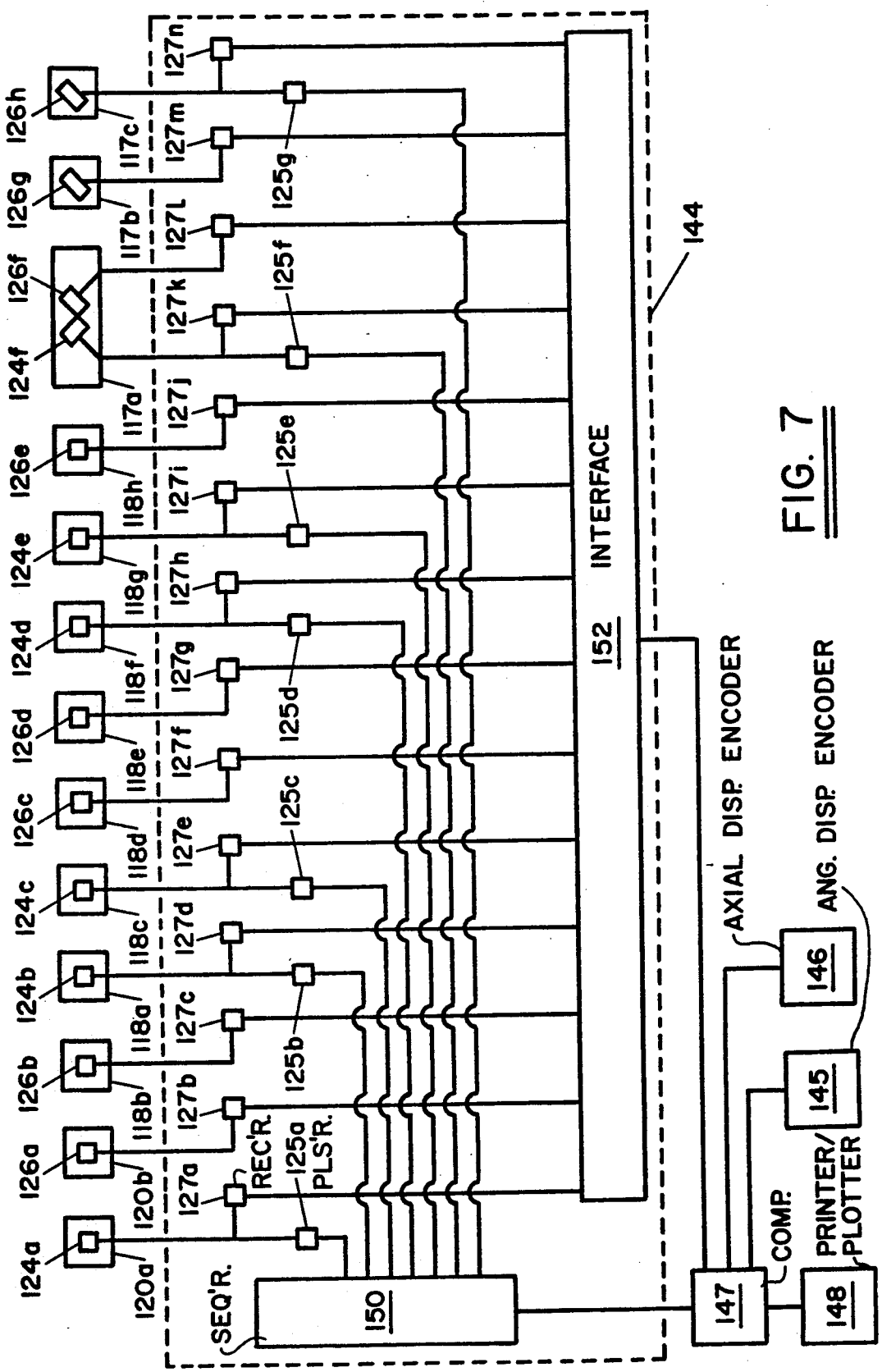
FIG. 7 is a schematic representation of the entire ultrasonic inspection device employing the module shown in FIG. 4.

FIG. 7 is a simplified schematic illustration of a single mode ultrasonic inspection device embodying the principles of the invention and adapted for use with the alternate module 110 shown in FIG. 4. In addition to the search units 117a-c, 118a-h, and 120a-b mounted on the module 110 shown in FIG. 4, the device in FIG. 7 includes a multiplexer circuit 144, axial and angular displacement encoders 145 and 146, a digital computer 147, and a printer or plotter 148. The multiplexer circuit 144 includes individual receiver circuits 127a-n, one for each of the search units and two for search unit 117a, pulser circuits 125a-g, one for each source transducer on the module, a sequencer circuit 150, and a computer interface 152.

Referring to the right hand side of FIG. 7, the three axially aligned search units 117a-c house transducer elements in a similar arrangement to that shown in FIG. 3. Specifically, transducer shoe 117a includes a source transducer element 124f and a catch transducer element 126f. Each element 124f and 126f is oriented for directing or receiving shear mode ultrasonic signals axially into the rotor material (not shown in FIG. 7) along a common plane. Search unit 117b includes a catch transducer element 126g oriented to detect ultrasonic signals reflected from the search signals transmitted from transducer element 124f within a certain depth range within the rotor material. Also, search unit 117c includes a catch transducer element 126h oriented to detect signals reflected from the transducer 124f search signals in yet a deeper range below the bore surface.

Unlike the transducer arrangement shown in FIG. 3, the source transducer 124f shown in FIG. 7 is also connected to a receiver circuit 127k. Thus the source transducer 124f is capable of operating to send and receive ultrasonic signals, and therefore produce pulse/echo information, and also to produce pitch signals for the catch transducers 126f-h. Also, the catch transducer 126h is connected to a pulser circuit 125g in addition to the receiver circuit 127n. Thus the transducer 126h may be operated to produce shear mode pulse/echo information in an axial direction opposite to that of transducer 124f. As with the dual function source transducers 124a and 124b described with reference to FIGS. 5 and 6 the transducer 124f and its catch transducers may be operated to provide both pitch/catch information and pulse/echo information from a common incident ultrasonic search signal.

In operation, the alternate search module 110 is first connected to drive shaft 111 and the remainder of the position determining means such as that shown at 14 in FIG. 1. The electrical connections between the multiplexer 144 and the transducers on the module 110 are made through a suitable slip ring capable of handling the required number of conductors, similar to the slip ring 49 shown in FIG. 1.

As the module 110 is spiraled through a rotor bore by the drive means the sequencer circuit 150 shown in FIG. 7 is operated to fire or trigger the source transducers 124a-f and transducer 126g in a desired sequence or pattern. Thus, the source transducers 124a-f and transducer 126g periodically transmit shear mode ultrasonic search signals into the rotor material. Since the module is continuously rotating and advancing, the frequency of the transmitted signals is chosen in light of the signal beam width, to ensure complete coverage of the rotor material.

As acoustic discontinuities in the rotor material are encountered, some of the ultrasonic search signal energy is reflected back to the source transducer, to a catch transducer, or both. The detected ultrasonic signals are converted into electrical pulses by the receiving transducer and the pulses are then received and conditioned by the respective receiver circuit 127a-n. The conditioned signals are then directed to the interface 152 where they may be rapidly inputted to the computer 147 for storage, and when desired, for display on the computer monitor or on a hard copy produced by the printer/plotter 148. Meanwhile, the angular and axial displacement encoders 145 and 146, respectively, continuously input to the computer both the position of the transmitting transducers and the position of the receiving transducers. Thus, the device shown in FIG. 7 produces both pulse/echo and pitch/catch information using only shear mode ultrasonic signals. The shear mode pulse/echo and pitch/catch information may then be correlated and combined to characterize the acoustic discontinuities in the rotor material.

The above-described preferred embodiments are intended to illustrate the principles of the invention, but not to limit the scope of the invention. Various other embodiments and modifications may be made by those skilled in the art without departing from the scope of the following claims.

We claim:

1. A method of inspecting the volume of an object comprising the steps of:
   (a) transmitting shear mode ultrasonic search signals into the mass of the object from an inspection surface thereof so that the search signals propagate along a plane extending substantially normal to the inspection surface, the search signals being transmitted with a source transducer;
   (b) detecting shear mode ultrasonic catch signals at at least one of a plurality of catch transducers aligned along the inspection surface on the plane along which the search signals propagate, the catch signals being produced as the search signals encounter discontinuities in the mass of the object and a portion of their energy is directed back toward the inspection surface, each catch transducer detecting shear mode ultrasonic catch signals produced within a substantially different depth range below the inspection surface;
   (c) determining the position of the source transducer and the catch transducers so that the shear mode ultrasonic search signals transmitted by the source transducer and the shear mode ultrasonic signals detected by the catch transducers may be correlated;
   (d) for each signal detected by one of the catch transducers, determining the time interval between the receipt of said catch signal and the transmission of the ultrasonic search signal from which said received catch signal is produced;
   (e) recording the shear mode ultrasonic catch signals detected at the catch transducers so that the catch signals may be analyzed to gain information regarding the acoustic discontinuities in the mass of the object to be inspected; and
   (f) recording the position of the source transducer and each catch transducer at each point that an ultrasonic signal is detected by one of the catch transducers.

2. The method of claim 1 including the step of:
   (a) detecting at the source transducer shear mode ultrasonic echo signals that are produced as the ultrasonic search signals therefrom encounter acoustic discontinuities in the mass of the object and a portion of their energy is directed back toward the source transducer.

3. The method of claim 2 wherein:
   (a) the echo signals detected at the source transducer and the catch signals detected at at least one of the plurality of catch transducers are produced from a common ultrasonic search signal.

4. The method of claim 1 wherein the object being inspected has a generally cylindrical bore and the shear mode ultrasonic search signals are transmitted along a plane extending generally radially from the longitudinal axis of the object bore, and further including the steps of:
   (a) transmitting shear mode circumferential search signals from the bore surface with a plurality of circumferential source transducers spaced out axially along the bore surface, the circumferential search signals from each circumferential source transducer propagating along a different plane extending generally perpendicular to the longitudinal axis of the bore; and
   (b) detecting shear mode circumferential catch signals at one or more of a plurality of circumferential catch transducers, each circumferential catch transducer aligning with a different one of the circumferential source transducers to form a pitch-/catch pair therewith and each circumferential catch transducer adapted t detect circumferential catch signals produced within a substantially different depth range below the bore surface.

5. The method of claim 4 including the step of:
   (a) detecting at one of the circumferential source transducers shear mode circumferential echo signals that are produced as the circumferential search signals therefrom encounter acoustic discontinuities in the mass of the object and a portion of their energy is directed back toward said one of the circumferential source transducers.

6. An ultrasonic inspection apparatus comprising:
   (a) transmitting means, including a source transducer, for transmitting shear mode ultrasonic search signals from the source transducer into the mass of an object from an inspection surface thereof so that the search signals propagate along a plane extending normal to the inspection surface;
   (b) signal receiving means, including a plurality of catch transducers aligned along the normal plane along which the search signals propagate, for receiving shear mode ultrasonic catch signals that are produced as the ultrasonic search signals encounter acoustic discontinuities in the mass of the object to be inspected and a portion of their energy is directed back toward the inspection surface, each catch transducer receiving shear mode ultrasonic catch signals produced within a substantially different depth range below the inspection surface;
   (c) position determining means for determining the position of the source transducer and each catch transducer so that the shear mode ultrasonic search signals transmitted by the source transducer and the shear mode ultrasonic catch signals detected by each catch transducer may be correlated; and
   (d) recording means for recording the shear mode catch signals received by the signal receiving means, along with the time interval between the receipt of each catch signal and the transmission of the shear mode ultrasonic search signal from which each said catch signal is produced, and the position of the source transducer and each catch transducer.

7. The apparatus of claim 6 wherein:
   (a) the signal receiving means is also for receiving at the source transducer shear mode ultrasonic echo signals that are produced as search signals from the source transducer encounter acoustic discontinuities in the mass of the object and a portion of their energy is directed back toward the source transducer.

8. The apparatus of claim 7 wherein:
   (a) the signal receiving means is adapted for receiving ultrasonic catch signals and ultrasonic echo signals that are produced when a common ultrasonic search signal encounters acoustic discontinuities in the mass of the object.

9. The ultrasonic inspection apparatus of claim 6 wherein the object to be inspected includes an elongated cylindrical bore and wherein:
(a) the signal transmitting means includes a plurality of circumferential source transducers spaced out axially along the bore, each adapted to direct shear mode ultrasonic search signals circumferentially from the object bore into the mass of the object along a different plane extending generally perpendicular to the longitudinal axis of the bore; and
(b) the signal receiving means includes a circumferential catch transducer for each circumferential source transducer, each circumferential catch transducer positioned along a different one of the places along which the circumferential search signals propagate so as to form a pitch/catch pair with a different one of said plurality of circumferential source transducers and adapted to detect circumferential catch signals from a different depth range below the surface of the object bore.

10. The ultrasonic inspection apparatus of claim 9 wherein:
(a) one of the plurality of circumferential source transducers is adapted to receive circumferential echo signals produced as the circumferential search signals therefrom encounter discontinuities in the mass of the object and a portion of their energy is directed back toward said one of the circumferential source transducers.

11. An ultrasonic inspection apparatus for inspecting the mass of an object having an elongated and generally cylindrical bore extending therethrough, the inspection apparatus comprising:
(a) transmitting means, including a plurality of circumferential source transducers spaced out axially along the bore, for transmitting from each of the circumferential source transducers shear mode ultrasonic search signals circumferentially from the object bore into the mass of the object along a different plane extending generally perpendicular to the longitudinal axis of the bore;
(b) signal receiving means including a circumferential catch transducer for each circumferential source transducer positioned along a different one of the planes along which the circumferential search signals propagate so as to form a pitch/catch pair with a different one of said plurality of circumferential source transducers, the signal receiving means for receiving shear mode circumferential catch signals that are produced as the circumferential search signals encounter acoustic discontinuities in the mass of the object to be inspected and a portion of their energy is directed back toward the object bore, each circumferential catch transducer adapted for detecting circumferential catch signals from a substantially different depth range below the surface of the object bore;
(c) position determining means for determining the position of each of the circumferential source and catch transducers so that the circumferential search signals and the circumferential catch signals may be correlated; and
(d) recording means for recording the circumferential catch signals received by the signal receiving means, along with the time interval between the receipt of each circumferential catch signal and the transmission of the circumferential search signal from which each said circumferential catch signal is produced, and the position of each circumferential source and catch transducer.

12. The ultrasonic inspection apparatus of claim 11 wherein:
(a) one of the plurality of circumferential source transducers is adapted to receive circumferential echo signals produced as the circumferential search signals therefrom encounter discontinuities in the mass of the object and a portion of their energy is directed back toward said one of the circumferential source transducers.

* * * * *

UNITED STATES PATENT AND TRADEMARK OFFICE
CERTIFICATE OF CORRECTION

PATENT NO. : 5,189,915

DATED : March 2, 1993

INVENTOR(S) : Reinhart et al.

It is certified that error appears in the above-identified patent and that said Letters Patent is hereby corrected as shown below:

Column 14, line 11 delete "t" and replace with --to--.

Signed and Sealed this

Twelfth Day of July, 1994

*Attest:*

BRUCE LEHMAN

*Attesting Officer*     *Commissioner of Patents and Trademarks*